(12) United States Patent
Gennari et al.

(10) Patent No.: US 9,265,793 B2
(45) Date of Patent: Feb. 23, 2016

(54) COMPOSITIONS WITH ANTIBACTERIAL AND WOUND HEALING ACTIVITY

(75) Inventors: Giovanni Gennari, Abano Terme (IT); Giampaolo Menon, Abano Terme (IL); Susi Panfilo, Abano Terme (IT)

(73) Assignee: FIDIA FARMACEUTICI S.p.A, Abano Terme (PD) (IT)

( * ) Notice: Subject to any disclaimer, the term of this patent is extended or adjusted under 35 U.S.C. 154(b) by 453 days.

(21) Appl. No.: 13/988,285

(22) PCT Filed: Nov. 4, 2011

(86) PCT No.: PCT/IB2011/054923
§ 371 (c)(1),
(2), (4) Date: May 17, 2013

(87) PCT Pub. No.: WO2012/066447
PCT Pub. Date: May 24, 2012

(65) Prior Publication Data
US 2013/0230594 A1 Sep. 5, 2013

(30) Foreign Application Priority Data
Nov. 19, 2010 (IT) .................................. PD10A0349

(51) Int. Cl.
A61K 31/728 (2006.01)
A61K 33/38 (2006.01)
A61K 9/00 (2006.01)
A61K 47/36 (2006.01)

(52) U.S. Cl.
CPC ............ *A61K 31/728* (2013.01); *A61K 9/0014* (2013.01); *A61K 33/38* (2013.01); *A61K 47/36* (2013.01)

(58) Field of Classification Search
None
See application file for complete search history.

(56) References Cited

U.S. PATENT DOCUMENTS

2011/0097281 A1    4/2011   Neubourg

FOREIGN PATENT DOCUMENTS

| DE | 102005008299 A1 | 12/2006 |
| DE | 102007044583 A1 | 4/2009 |
| DE | 102008031023 A1 | 12/2009 |
| WO | WO-87/05517 A1 | 9/1987 |
| WO | WO-95/03786 A2 | 2/1995 |
| WO | WO-96/35720 A1 | 11/1996 |
| WO | WO-02/18448 A2 | 3/2002 |
| WO | WO-2008/031601 A1 | 3/2008 |
| WO | WO-2010/051918 A2 | 5/2010 |
| WO | WO-2010/127647 A1 | 11/2010 |

OTHER PUBLICATIONS

Barbucci, R. et al., "Cu2+- and Ag+-complexes with a hyaluronane-based hydrogel," Journal of Materials Chemistry, The Royal Society of Chemistry, Cambridge, GB, vol. 12, No. 10, Oct. 1, 2002, pp. 3084-3092.
Journal of Biomedical Materials Research, Part A Sep. 15, 2009 LNKD-Pubmed:18671256, vol. 90, No. 4, Sep. 15, 2009,pp.1177-1185.
Investigate Ophthalmology & Visual Science Jun. 1993 LNKD-Pubmed:8505213, vol. 34, No. 7, Jun. 1993, pp. 2313-2315.

*Primary Examiner* — Robert A Wax
*Assistant Examiner* — Randeep Singh
(74) *Attorney, Agent, or Firm* — Birch, Stewart, Kolasch & Birch, LLP

(57) ABSTRACT

The present invention relates to compositions based on silver and hyaluronic acid and their use in the management of cutaneous lesions of various origin (acute and chronic wounds, ulcerations, burns, etc.) mainly when characterized by the presence of exudate and hence at high risk of infection.

23 Claims, 3 Drawing Sheets

COMPOSITIONS WITH ANTIBACTERIAL AND WOUND HEALING ACTIVITY

This application is the National Phase Under 35 U.S.C. §371 of PCT International Application No. PCT/IB2011/054923 which has an International filing date of Nov. 4, 2011, which claims priority to Italian Application No. PD2010A000349 filed on Nov. 19, 2010. The entire contents of all applications listed above are hereby incorporated by reference.

FIELD OF THE INVENTION

The present invention relates to a composition based on silver and hyaluronic acid, to a pharmaceutical formulation comprising said composition, to its use in the treatment of cutaneous lesions and wounds and to an apparatus comprising said composition.

BACKGROUND OF THE INVENTION

Acute or chronic cutaneous lesions of various origin are managed by application of medical devices to aid wound healing, promote revascularization, absorb exudate and, where necessary, exert an antibacterial/antimicrobial action.

Normally, exudate is the consequence of the increased permeability of capillaries in the inflammatory tissue. Exudate has the task to confine the pathological process, preventing the diffusion of microorganisms and blocking the action of possible dangerous antigens through an immune mechanism.

On the contrary, in chronic lesions exudate is produced in an abnormal way and it determines a blockage of the process of tissue repair by destruction of the proteins of the extracellular matrix and growth factors, and by inhibition of cell proliferation. Clinically, hyperexudation can determine maceration of perilesional skin and promote infection, in particular by the bacterial species *Escherichia coli*, *Pseudomonas aeruginosa*, *Enterococcus faecium*, *Staphilococcus aureus* and by fungi such as *Candida albicans*.

Additionally, hyperproduction of exudate results in the need for continuous replacement of the wound dressings. In these situations, neither the discomfort felt by the patient who sees his/her quality of life worsened by the constant need of healthcare nor the consequent increase of health costs should be underestimated.

Today, numerous devices containing antibacterial agents are commercially available and have different characteristics depending on the application they are intended for. Among the others, foams, adhesive or not, based on polyurethane and hydrocolloid (Contreet®) or based on hydrofiber (Aquacel Ag); multilayer polyethylene nets (Acticoat®). Gauzes containing absorbent powders should be mentioned. These products are characterized by an absorbent polymeric support and a metal, in particular silver. The antibacterial properties of silver are well known (Fraser, J. F. et al. *ANZ J. Surg.* 2004, 74, 139-212) and are generally related to the oxidized form of ionic silver. Silver inhibits the synthesis of structural proteins composing the bacterial wall preventing its formation, and binds to enzymatic proteins of bacterial DNA, disrupting its functionality. However, such bindings occur in an aspecific way, that is silver acts both on bacterial cells present in the wound and on surrounding cutaneous/dermic cells, which results in toxicity of silver for the wounded patient. In fact, silver inhibits proliferation of keratinocytes and fibroblasts (fundamental components of dermis and epidermis), slowing down the regeneration of the wound bed on which it is applied, and this is detrimental to complete healing of the lesion, insomuch that from the results of some in vitro tests on keratinocyte cultures, some go as far as recommending to avoid the application of silver based devices (Lam, P. K. et al. *Br. J. Biomed. Sci.*, 2004, 61, 125-127). Additionally, silver is a sensitizing agent, mainly when applied for long periods, exactly as it occurs in the case of decubitus ulcers, burns, or slow healing wounds in general ("*Chronic exposure to Silver or Silver salts, Patty's Industrial Hygiene and Toxicology*", Vol. 2, G. D. Clayton, F. E. Clayton, Eds. Wiley-Interscience, New York, 3rd Ed., 1981, p. 1881-1894).

Hyaluronic acid (HA) is a heteropolysaccharide, i.e. a polymer, that can have a wide range of molecular weights, generally correlated to different biological effects.

The multiplicity of biological effects of the HA is well known, and is essentially bound to its chemical nature.

High MW fractions (of the order of millions of Daltons) have very high viscosity and find specific application in ocular surgery and also in particular cases of soft tissue filling, for both surgical and dermocosmetic purposes; the effect on wound healing, instead, is strongly controversial insomuch that some authors have demonstrated very positive effects on cell proliferation by high mean MW HA, while others have highlighted exactly the opposite effect.

Intermediate molecular weight fractions (500-750 kDa) (Brun et al. *Osteoarthritis Cartilage*, 2003, 11, 208-16) are normally used as viscosupplements in osteoarthrosis and joint diseases in general. Because they may generate solutions with viscosity which is very similar to that of the synovial fluid, in fact, these fractions exert a mechanical lubrication action. Last, low molecular weight HA (oligomeric HA, generally meant as having mean MW comprised between 1 and 10 kDa) has remarkable angiogenic action; thus it particularly promotes revascularization of the tissues on which it is applied, promoting wound healing. Additionally, low molecular weight HA has the known ability of stimulating cell mobility and activating fibroblast migration, which is obviously of great importance for repairing processes (West et al., *Science*, 1985, 228, 1324-6; Deed et al., *Int. J. Cancer*, 1997, 71, 251-6). For these reasons, low molecular weight HA is employed as a component of numerous products and devices with wound healing action. One of the objects of the invention is to provide a composition for wound dressing and healing that is more efficient and less toxic than those presently available for the treatment of skin lesions Another object of the invention is to meet the clinical need of dressings with a strong antimicrobial/antifungal active agent while minimizing inhibitory effects on tissue regeneration and toxicity on the tissues to be treated.

SUMMARY OF THE INVENTION

The present invention provides a composition comprising hyaluronic acid and silver, wherein hyaluronic acid has an average weight molecular weight between 130 and 230 Kda and wherein silver has a colloidal metallic form or a micronized metallic form with a porous "sponge like" structure.

The present invention also provides a pharmaceutical formulation comprising said composition and at least one pharmaceutically acceptable excipient.

Also disclosed is the use of said composition as a medicament, in particular for the topical treatment of superficial and/or of small cavity cutaneous lesions and/or of wounds.

The present invention also relates to an apparatus for dispensing said composition in the form of a dry spray, a foam or a hydrophilic gel, which are suitable for cutaneous application.

DETAILED DESCRIPTION OF THE INVENTION

Figure 1:
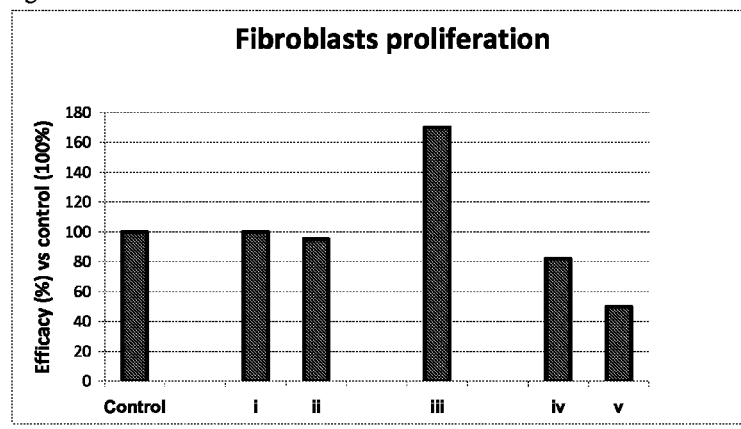
FIG. 1 shows the evaluation (Experiment 1) of the in vitro cell proliferation of human fibroblasts cultured in the presence of HA with different weight average molecular weight fractions ranging from 5000-10000 Da (sample i) to 1,500,000-3,200,000 Da (sample v).

As used herein, the term "weight average molecular weight" is intended as calculated with the "intrinsic viscosity" method (Terbojevich et al., *Carbohydr. Res.*, 1986, 363-377).

As used herein, "sponge like structure" is intended as a fully porous material, with open cell and/or closed cell structure, with surface area of 5 m$^2$/g or higher.

In one embodiment, the present invention relates to a composition comprising hyaluronic acid and silver, wherein hyaluronic acid has an average weight molecular weight between 130 and 230 Kda and wherein silver has a colloidal metallic form or a micronized metallic form with a porous "sponge like" structure.

The composition disclosed herein promotes healing of lesions of various kinds (acute, chronic, ulcerations of various aetiology, burns, sores) eliminating bacterial and/or fungal infections and promoting healing of the damaged tissue. It was surprisingly found that these advantages are obtained with a composition comprising hyaluronic acid having a well defined mean weight molecular weight (MW) that, as it disclosed herein, stimulates human fibroblast proliferation, with consequent deposition of collagen and fibronectin, and is protective against the damages that silver may produce on these cells.

The antibacterial activity of the composition known in the art is performed by silver, commercially available in the form of salts (e.g. nitrate, sulfate, carbonate and others, available e.g. from Sigma Aldrich), or colloidal metal, i.e. associated to small proteins that improve its stability, or in a metallic form.

Among the various types of metallic silver, it was surprisingly found as particularly suitable micronized metallic silver with the following characteristics:

mean particle size 2-18 micrometers, preferably 10 micrometers

"sponge like" (SL) microstructure with high porosity which considerably increases superficial area ($\geq 5$ m$^2$/g);

high purity (preferably >99.5%);

(hereafter "sponge like micronized metallic silver").

Said peculiar "sponge like" porous structure promotes an enhanced release, both immediate and sustained, of Ag ions (Ag$^+$) in the wound bed, which results in increased antimicrobial and antifungal activity compared to the forms of silver which are most commonly used, as demonstrated by the results of the experiments hereafter.

Notably, "sponge like" micronized metallic silver as comprised in the composition of the invention does not stain skin and clothes, also after exposure to sunlight, does not dye the wound brown when exudate is present and is easier to handle in the preparation of pharmaceutical forms according to the invention. The micro-scale particle size renders "sponge like" micronized metallic silver readily mixable with other components. Colloidal metallic silver, instead, must undergo a micronization process first, especially when delivery in the form of a spray is desired, in order to prevent obstructions due to the formation of clumps of powder.

Silver used for the composition of the present invention can be colloidal or "sponge like" micronized metallic silver, which were found to have comparable antibacterial/antimicrobial activity, although "sponge like" micronized metallic silver is preferable.

Hyaluronic acid (HA) is a linear chain heteropolysaccharide composed of alternate D-glucuronic acid and N-acetyl-D-glucosamine residues, with weight average molecular weight that can range between 400 and 3×10$^6$ Da, depending on the extraction source or the method of preparation employed. Hyaluronic acid, in fact, can be obtained for example by extraction from cockscombs (EP 138 572 B1), by fermentation, or synthetic means. As already said, it is known that HA exerts a multiplicity of roles within the body, ranging from mechanic support for the cells of many tissues such as skin, tendons, muscles and cartilage, to hydration of tissues and lubrication of joints. Furthermore, it is known that HA, through its membrane receptor CD44, is able to modulate many and different processes related to cellular physiology and biology such as cell proliferation, migration, differentiation and angiogenesis.

Each of these effects is essentially attributable to fractions of HA with different molecular weights, and particularly the action of tissue repair is remarkably evident in HA fractions with low weight molecular weight (oligomeric HA) and decreases as the molecular weight increases. Over several tests, instead, it was surprisingly found that a particular fraction of HA with weight average MW comprised in a range between 130 and 230 kDa, calculated with the "intrinsic viscosity" method (Terbojevich et al., Carbohydr. Res., 1986, 363-377), hence having a MW markedly higher than those already known for their wound healing action, has an extraordinary effectiveness towards human fibroblast proliferation. In addition, it was found that HA with weight average molecular weight between 130 and 230 kDa surprisingly improves the antimicrobial/antifungal activity of silver (colloidal metallic form or "sponge like" micronized metallic form) it is associated with, dramatically reducing its cytotoxicity. Such HA fraction, after suitable tests, was selected for the compositions object of the present invention, of which it is demonstrated, through the experiments described herein, both efficacy against pathogens over standard treatments and reduction of toxicity against human fibroblasts, with consequent increase of the wound healing activity. Remarkably, the HA used in the compositions of the present invention can originate from an extractive, fermentation (from *Streptococ-*

*cus*) or biosynthetic (from *Bacillus*) source, preferably from a fermentation or biosynthetic source, and has a weight average MW comprised between 130 and 230 kDa, preferably between 145 and 210 kDa and even more preferably between 160 and 200 kDa; the latter for short will be hereinafter defined as 160-200 kDa weight average MW HA. It can be purchased from numerous firms (for example, Lifecore Biomedical; QP Corp.; Seikagaku; Shiseido; Fidia farmaceutici) that are able to provide HA with the desired specifications concerning MW.

Contrary to the expectations, it was found that fractions of hyaluronic acid having weight average molecular weight markedly higher than that of oligomeric fractions have stronger positive influence on fibroblast proliferation than that of oligomeric fractions. The composition comprising these specific fraction of HA and silver demonstrates an improvement of antibacterial/antifungal effect and also a reduced toxicity against fibroblasts in comparison with standard compositions based on silver alone in specific tests.

Figure 4:
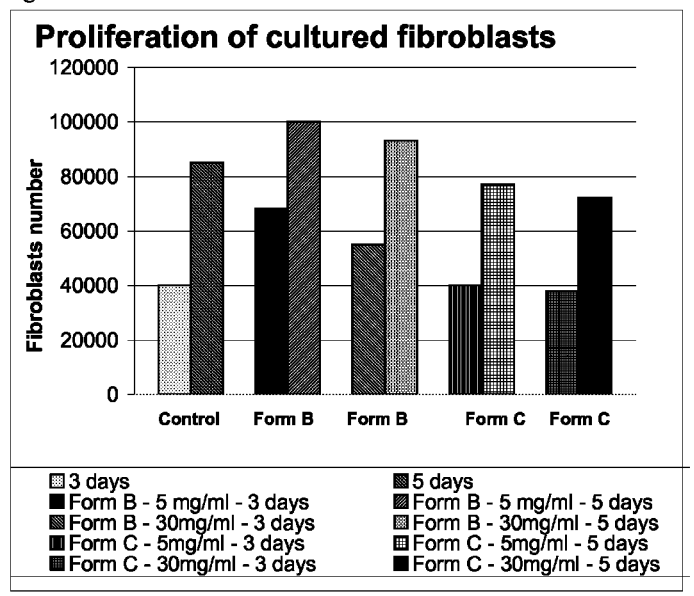
FIG. 4 shows the effects on proliferation of healthy fibroblasts of compositions of the invention comprising colloidal metallic silver (A) and micronized metallic silver (B) compared with a control and a commercially available formulation comprising colloidal metallic silver which does not comprise hyaluronic acid (C) at concentrations of 5 and 30 mg/ml after 3 or 5 days of culture.

For example, with reference to FIG. 4 third column, the composition of the invention, comprising these specific fraction of HA and silver, stimulates growth of fibroblast with respect to the control sample whereas a reduction of fibroblasts with respect to the control is observed using colloid silver, without HA, in an overall amount as low as one third of that in the test with the composition of the invention.

This means that the composition of the present invention represents a clear and unpredictable progress over the state of the art, being more efficient and less toxic than the compositions currently available for the topic treatment of the described cutaneous lesions.

Based on the results of the experiments disclosed hereafter, it was unexpectedly found that the composition of the invention which comprises HA with weight average molecular weight 160-200 kDa and colloidal or micronized "sponge like" metallic silver has the following surprising properties:

an unprecedented and remarkable capacity by HA with weight average molecular weight 160-200 kDa to stimulate fibroblasts proliferation;

antibacterial activity, related to the presence of colloidal silver or micronized "sponge like" metallic silver, which is at least comparable to that of conventional treatments against microorganisms generally found in infected wounds;

in particular when micronized "sponge like" metallic silver is used, the composition of the invention is more active that the standard treatments against MRSA, which is particularly difficult to contrast;

very low or absent toxicity towards cutaneous fibroblasts;

antibacterial activity exerted also in the presence of amounts of silver lower than 50% of the formulation available on the market, while maintaining the capacity of HA to stimulate fibroblasts proliferation.

For these reasons, the composition of the invention is particularly advantageous over the compositions known in the prior art and over the compositions currently available for treatment of cutaneous lesions and wounds originating, for example, from cutaneous lesions and/or wounds of various origin (acute, chronic, ulcerations of various aetiology, burns, sores).

Preferably, in the composition of the invention hyaluronic acid has an average weight molecular weight between 145 and 210 Kda.

Preferably, in the composition of the invention hyaluronic acid has an average weight molecular weight between 160 and 200 Kda and silver has a micronized metallic form with a porous "sponge like" structure.

Preferably, in the composition of the invention silver with a micronized metallic form with a porous "sponge like" structure has a mean particle size between 2 and 18 micrometers and a surface area not less that 5 $m^2/g$.

Preferably, in the composition of the invention hyaluronic acid has a concentration between 0.1 and 2% w/w of the total composition, more preferably between 0.1 and 0.5% w/w of the total composition and yet more preferably 0.2% w/w of the total composition.

Preferably, in the composition of the invention silver in a colloidal metallic form or silver in micronized metallic form with a porous "sponge-like" structure has a concentration between 1 and 3% w/w of the total composition, more preferably 2% w/w of the total composition.

A composition according to the present invention can be in the form of powders, solutions or suspensions, to be dispensed under various forms, among which hydrophilic gel, foam, dry spray are preferred, as they exhibit some particularly desired characteristics. In particular, dry spray and foam:

are readily applicable without particular operations, as they need neither cutting nor shaping to adapt to the wound;

can be applied avoiding contact with the wound, contributing in this way to reduce additional contamination causes;

are perfectly adaptable to the site on which they will be applied, that is, a superficial, flat or anyway little cavitated wound will benefit from the application of a dry spray, which will be easily evenly distributed. In fact, the hyaluronic acid powder present in the dry spray, in contact with the exudate, immediately forms a clear gel that keeps the cavity of the lesion moist at an extent that promotes wound healing and at the same time divides it from the surrounding environment, preventing additional contaminations; in a deep, hollow wound, it will be more useful to apply a foam instead, which homogeneously and evenly fills the whole wound bed, promoting intimate contact of both wound healing (hyaluronic acid) and antibacterial agent (silver) with the lesioned part;

do not necessarily require to be covered with bandages, with the advantage of simplifying the dressing renewal step.

Concerning the form of hydrogel, it finds specific application in case of not particularly deep nor cavitated wounds and with little exudate; in fact, the hydrogel itself provides the environment with correct moisture that is fundamental for the healing process.

In one embodiment, the present invention provides a pharmaceutical formulation comprising a composition comprising hyaluronic acid and silver, wherein hyaluronic acid has an average weight molecular weight between 130 and 230 Kda and wherein silver has a colloidal metallic form or a micronized metallic form with a porous "sponge like" structure, and at least one pharmaceutically acceptable excipient.

Preferably, the pharmaceutical formulation of the present invention further comprises at least one excipient selected from a suspending agent, a vehicle and a propellant.

More preferably, in the pharmaceutical formulation according to the present invention the propellant is selected from a group consisting of isobutane/n-butane/propane mixtures and n-butane.

Preferably, the pharmaceutical formulation according to the invention is in the form of a dry spray, a foam or a hydrophilic gel, which are suitable for cutaneous application.

Preferably, the pharmaceutical formulation according to the invention is in the form of a dry spray which lays as transparent gel on the cavity of the lesion to promote the optimal moist wound healing.

More preferably, the pharmaceutical formulation according to the invention is in the form of a dry spray, comprising hyaluronic acid with an average weight molecular weight between 160 and 200 kDa with concentration 0.2% w/w, micronized metallic silver with a porous "sponge like" structure at concentration 2% w/w and n-butane as propellant.

More preferably, the pharmaceutical formulation according to the invention is in the form of a dry spray, comprising hyaluronic acid with a weight average molecular weight between 160 and 200 kDa with concentration 0.2% w/w, colloidal metallic silver with concentration 2% w/w and n-butane as propellant.

Preferably, the pharmaceutical formulation according to the invention is in the form of foam, comprising hyaluronic acid with a weight average molecular weight between 160 and 200 kDa with concentration 0.2% w/w, silver in metallic micronized form with a porous "sponge-like" structure or in a colloidal metallic form with a 2% w/w concentration and a isobutane/n-butane/propane mixture as propellant.

Preferably, the pharmaceutical formulation according to the invention is in the form of hydrophilic gel comprising hyaluronic acid with a weight average molecular weight between 160 and 200 kDa with concentration 0.2% w/w, silver in metallic micronized form with a porous "sponge-like" structure or in a colloidal metallic form with a 2% w/w concentration and a isobutane/n-butane/propane mixture as propellant.

In an embodiment, the present invention relates to a composition or a pharmaceutical formulation as disclosed above for use as a medicament.

In another embodiment, the present invention relates to a composition or a pharmaceutical formulation as disclosed above for use in the topical treatment of superficial and/or small cavity cutaneous lesions and/or wounds.

Preferably, the pharmaceutical formulation for use in the topical treatment of superficial and/or small cavity cutaneous lesions and/or wounds is in the form of a dry spray, comprising hyaluronic acid with an average weight molecular weight between 160 and 200 kDa with concentration 0.2% w/w, micronized metallic silver with a porous "sponge like" structure at concentration 2% w/w and n-butane as propellant.

Preferably, the pharmaceutical formulation for use in the topical treatment of superficial and/or small cavity cutaneous lesions and/or wounds according to the invention is in the form of a dry spray, comprising hyaluronic acid with a weight average molecular weight between 160 and 200 kDa with concentration 0.2% w/w, colloidal metallic silver with concentration 2% w/w and n-butane as propellant.

Preferably, the pharmaceutical formulation for use in the topical treatment of superficial and/or small cavity cutaneous lesions and/or wounds according to the invention is in the form of foam, comprising hyaluronic acid with a weight average molecular weight between 160 and 200 kDa with concentration 0.2% w/w, silver in metallic micronized form with a porous "sponge-like" structure or in a colloidal metallic form with a 2% w/w concentration and a isobutane/n-butane/propane mixture as propellant.

Preferably, the pharmaceutical formulation for use in the topical treatment of superficial and/or small cavity cutaneous lesions and/or wounds according to the invention is in the form of hydrophilic gel comprising hyaluronic acid with a weight average molecular weight between 160 and 200 kDa with concentration 0.2% w/w, silver in metallic micronized form with a porous "sponge-like" structure or in a colloidal metallic form with a 2% w/w concentration and a isobutane/n-butane/propane mixture as propellant.

In yet another embodiment, the present invention relates to a method of treating superficial and/or small cavity cutaneous lesions and/or wounds comprising topical application of the composition or of the pharmaceutical composition as disclosed above.

In an embodiment, the present invention relates to an apparatus for dispensing the composition as disclosed above in the form of a dry spray, a foam for cutaneous application or a hydrophilic gel.

All the experiments shown in the present application were carried out on healthy fibroblasts isolated from human skin biopsies, so as to reproduce as accurately as possible the pathologic situation found when applying the final product. Cell culture tests used a three-dimensional material as a support, to accurately imitate the wound bed that, although damaged, comprises a dermic, deeper layer and an epidermic, more superficial one.

Research protocols and materials used are reported herein.

Experiment 1

Evaluation of In Vitro Cell Proliferation of Human Fibroblasts Cultured in the Presence of HA with Different MWs Based on what is available at the state of the art, different HA samples are prepared, and in particular:
i. HA with weight average MW comprised between 5,000-10,000 Da, prepared as per example 1 of EP 868 437;
ii. HA with weight average MW comprised between 10,000-15,000 Da, prepared as per example 2 of EP 868 437;
iii. HA with weight average MW 160,000-200,000 Da;
iv. HA with weight average MW 1,000,000 Da, prepared as per example 1 of EP 535 200;
v. HA with weight average MW 1,500,000-3,200,000 Da, Hyalubrix® (Migliore et al., Arthr. Res. Ther., 2009, 11, R183);
all at the concentration of 1 mg/ml of culture medium.

Isolation of Healthy Fibroblasts from Human Skin Biopsies: briefly, after some washings in Phosphate Buffer Solution (PBS) additioned with antibiotics, the biopsy is freed from subcutaneous adipose tissue and cut in small strips, which are subjected to enzymatic digestion by the enzyme dispase for 30 min. At the end of the treatment, skin is separated from underlying dermis, which is digested with trypsin for 10 min; cells are then extracted by centrifugation.

Cell Culture: cells are cultured in vitro by seeding in DMEM culture medium supplemented with 20% fetal bovine serum (FBS), 1% penicillin/streptomycin (P/S) and 1% glutamine.

MTT Test: this assay quantitatively measures the presence of succinate-dehydrogenase activity in cultured cells; such activity, present only in the mitochondria of viable cells, is normally used as a marker to check metabolic activity, viability and thus growth of cultured cells. The test is based on conversion of the azolic dye MTT (3-(4,5-dimethylthiazol-2-yl)-2,5 diphenyltetrazolium bromide) from yellow to blue by succinate-dehydrogenase. The amount of blue dye (formazan) spectrophotometrically determined is proportional to the presence of succinate-dehydrogenase in the cell culture and then is proportional to the number of viable cells.

Cells are incubated with a 0.5 mg/ml MTT solution for 3 h. At the end of the incubation the dye is extracted from the cell with an extraction solution (90% isopropanol, 10% DMSO) and is read at the wavelength of 540/660 nm.

Operating Procedure: as said, cell proliferation tests were carried out using three-dimensional cultures and precisely seeding cells on non-woven Hyaff 11 (prepared as per example 2 of EP 618 817). This is the procedure of choice when the intent is to mimic in vivo fibroblastic proliferation, and that is in a dermis consisting of an extracellular three-dimensional matrix mainly formed of hyaluronic acid and collagen, in which cutaneous fibroblasts are inserted.

Fibroblasts isolated according to what previously said are seeded (60,000) on small pieces of non-woven material (1×1 cm) attached within adequate plates, and kept in culture for 24 h. Afterwards, different HA samples to test were added to the culture medium, and after 3 days of treatment, the MTT test was carried out to evaluate cell proliferation. The control consisted of fibroblasts not treated with HA.

Results: as clearly shown in FIG. 1, contrary to what described at the state of the art, low MW HA fractions do not stimulate cell proliferation. The 160-200 kDa weight average MW fraction, instead, has marked proliferating activity, while MWs higher than one million Da result totally inefficient, when not even toxic.

Figure 2:
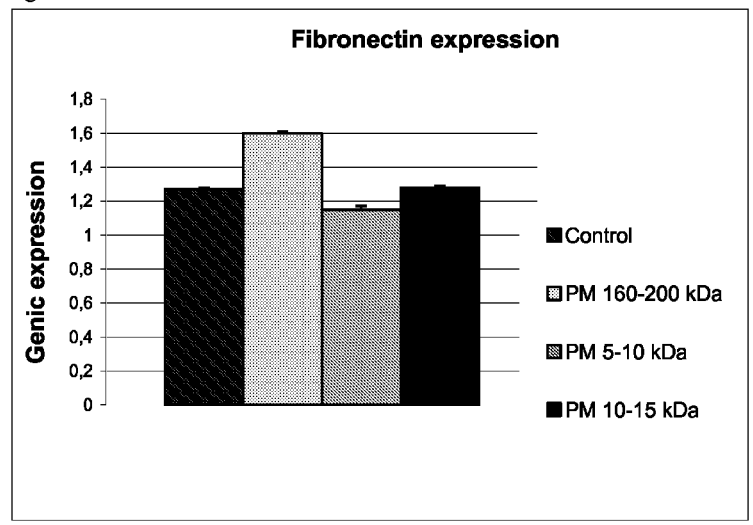
FIG. 2 shows the effect of HA with different weight average molecular weight fractions, namely 5000-10000 Da (sample i), 10,000-15,000 Da (sample ii) and 200,000 Da (sample iii) on fibronectin expression.
Figure 3:
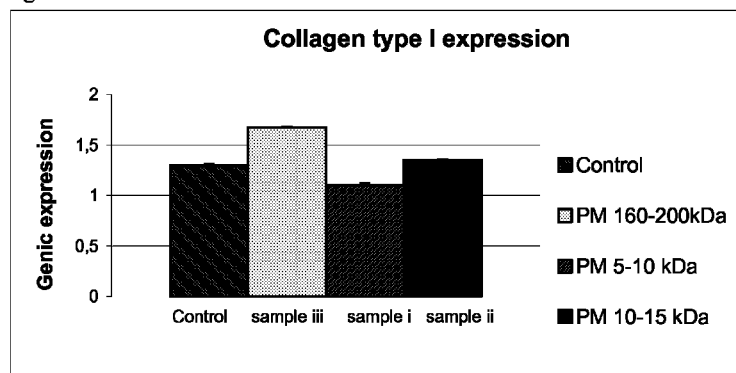
FIG. 3 shows the effect of HA with different weight average molecular weight fractions, namely 5000-10000 Da (sample i), 10,000-15,000 Da (sample ii) and 200,000 Da (sample iii) on collagen type I expression.

Proliferation and viability of fibroblasts are confirmed also by quantitative evaluation of genic expression of type I collagen (FIG. 3) and fibronectin (FIG. 2), according to the following procedure.

Fibroblasts were isolated and cultured as described above, and treated for 3 days with samples i, ii, iii (the others were excluded due to their negative effect on cell proliferation); at the end of the treatment Real Time PCR was carried out to evaluate genic expression of type I collagen and fibronectin: cellular RNA was extracted using the "Trizol" method, following the directions of the supplier (TRIZOL reagent, LIFE Techonologies, GIBCO BRL). Briefly, cells were lysed by adding 1.0 ml of Trizol and total RNA was quantified by measuring absorbance at 260 nm. For each gene to amplify, suitable primers were selected using the Primer3 software (Roche Molecular Diagnostics, Pleasanton, Calif., USA). Genic expression was evaluated by Real Time PCR carried out with Rotor-gene TM5500 (Corbett Research, Sydney, Australia). Results are summarized in FIGS. 2 and 3: they confirm that 160-200 kDa weight average MW HA determines a significant increase in genic expression of both proteins in comparison with control, and this means that treated fibroblasts are able to build extracellular matrix, essential for complete healing of wounds.

Conclusion: surprisingly, 160-200 kDa weight average MW HA exhibited an extraordinarily efficient action on cutaneous fibroblast proliferation. Such fibroblasts are viable and metabolically active since they depose extracellular matrix, therefore they are able to activate the repair of lesioned cutaneous tissues.

Based on the above unexpected results, the antimicrobial and antifungal effects of the formulations presented herein are evaluated using a marketed product as a control. Employed microorganisms are those normally present in infected wounds, i.e.: E. coli, P. aeruginosa, E. faecium (resistant to vancomycin), S. aureus (methicillin resistant) and C. albicans.

Test formulations, containing silver in both colloidal and metallic form, were prepared in the form of powder, to be dissolved in the experiment medium.

Experiment 2

Evaluation of Antimicrobial Antifungal Activity of the Preparations

Tests were performed in vitro, hence test formulations containing colloidal metallic or micronized metallic silver were prepared in the form of powders, so that they could be dissolved or suspended to evaluate their efficacy. The control formulation (C) is commercially available in the form of a powder, as well as of a dry spray (Katoxyn®, Devergè M&M).

Formulation A
0.2% Sodium HA MW 160-200 kDa
2% Colloidal metallic silver
4% Syloid 244 (excipient)
Light kaolin (excipient) q.s. to 100
Formulation B
0.2% Sodium HA MW 160-200 kDa
2% Micronized metallic silver sponge-like (SL) 2% (MicroSilver BG™ Pharma)
4% Syloid 244 (excipient)
Light kaolin (excipient) q.s. to 100
tested against a standard commercial composition (formulation C—Katoxyn®) consisting of
4.25% Colloidal metallic silver
1.5% Benzoyl peroxide
1% Anhydrous calcium gluconate (excipient)
Aluminium silicate (excipient) q.s. to 100

Test Microorganisms: a liquid culture of each microorganism was prepared following the directions of the supplier. Incubation lasted at least 48 h, so as to obtain a rich and viable culture; the title of each culture was approximately determined through the McFarland scale. For some microorganisms two test suspensions were prepared by inoculating in two 100 ml TSB samples (Tryptic Soy Broth; Millipore) an amount of liquid culture containing about $10^3$ and about $10^6$ CFU. Inoculates were then subjected to count to exactly determine the microbial content of the suspensions at T=0.

Formulations Samples: two samples of about 1 g were drawn from each formulation and were added to suspensions containing $10^3$ and $10^6$ CFU, or only $10^3$ CFU. So prepared samples were incubated and kept under constant slow shaking and vertical rotation, so as to maximize the intimate contact of the product with the microorganisms and to prevent the phenomenon of powder sedimentation. After 30 min of incubation, an aliquot was drawn, on which the count of the microbial content of the suspensions was carried out by the technique of the filtering membranes, by operating suitable dilutions on samples containing $10^6$ CFU. The membranes used for filtration were transferred in TSA medium (Tryptone Soy Agar—Biogenetics) and incubated for at least 5 days.

The count of the bacterial content in the test suspension was repeated after 12 h and 24 h.

The following tables disclose, for each tested formulation, the values of logarithmic reduction of the concentration of various microorganisms after different contact times.

TABLE 1

| Formulation A | | |
|---|---|---|
| | 12 hours | 24 hours |
| E. coli ATCC 8739 | | |
| $3 \times 10^3$ | 3 | 3 |
| $4 \times 10^5$ | 5 | 5 |
| P. aeruginosa ATCC 15442 | | |
| $6 \times 10^3$ | 3 | 3 |
| $5 \times 10^5$ | 5 | 5 |
| E. faecium ATCC 700221 | | |
| $2 \times 10^2$ | 2 | 2 |
| C. albicans ATCC 10231 | | |
| $5 \times 10^2$ | 2 | 2 |

From the data, it can be inferred that the bacterial content in all the inoculates treated with formulation A is practically nil after both 12 h and 24 h. This means that formulation A acts as a bactericide, and not as a bacteriostat. In fact, the European Pharmacopoeia defines a bactericide for topical use as a product that, after 24 h in contact with the microorganism, reduces its content by at least 2 logarithms of concentration.

TABLE 2

Formulation B

| | 12 hours | 24 hours |
|---|---|---|
| *E. coli* ATCC 8739 | | |
| $3 \times 10^3$ | 3 | 3 |
| $4 \times 10^5$ | 5 | 5 |
| *P. aeruginosa* ATCC 15442 | | |
| $6 \times 10^3$ | 3 | 3 |
| $5 \times 10^5$ | 5 | 5 |
| *E. faecium* ATCC 700221 | | |
| $2 \times 10^2$ | 2 | 2 |
| *C. albicans* ATCC 10231 | | |
| $5 \times 10^2$ | 2 | 2 |

Formulation B has an activity profile identical to that of formulation A. This means that the activity on the microorganisms in this experiment of silver formulated in association with hyaluronic acid is quali/quantitatively identical either in colloidal form or in "sponge like" micronized metallic form.

TABLE 3

Formulation C

| | 12 hours | 24 hours |
|---|---|---|
| *E. coli* ATCC 8739 | | |
| $3 \times 10^3$ | 3 | 3 |
| $4 \times 10^5$ | 5 | 5 |
| *P. aeruginosa* ATCC 15442 | | |
| $6 \times 10^3$ | 3 | 3 |
| $5 \times 10^5$ | 5 | 5 |
| *E. faecium* ATCC 700221 | | |
| $2 \times 10^2$ | 2 | 2 |
| *C. albicans* ATCC 10231 | | |
| $5 \times 10^2$ | 2 | 2 |

It appears evident that also formulation C reproduces the results seen with formulations A and B, but the data obtained give rise to an absolutely unexpected picture, taking into account some fundamental differences between the different formulations:
- A and B contain a concentration of silver (2%) clearly lower (less than a half) than that of C (4.25%)
- C contains benzoyl peroxide (BP); as all the peroxides, BP is an oxidizing agent per se, which is very often used in topical preparations against acne exactly for its ability to kill microorganisms due to the oxygen released from it. The activity of formulation C is thus due to silver and to BP contained in it, wherein BP acts on one side as an activator of silver oxidation, and on the other side as a source of an antibacterial agent, namely oxygen.

Conclusion: all the tested formulations can be defined, as per European Pharmacopoeia, bactericidal agents for topical use. In terms of reduction of the bacterial content the three preparations are qualitatively but not quantitatively equivalent, because, absolutely unpredictably, formulations A and B, comprising hyaluronic acid with weight average MW equal to 160-200 kDa, contain less than a half the silver present in C.

Formulations A and B are therefore more efficient than formulation C since they induce the same antibacterial antifungal effect with a concentration of silver markedly lower and without the aid of additional active agents (oxygen released from benzoyl peroxide).

Experiment 2a in view on the above data, an additional test is performed to evaluate the effect of compositions A, B and C (defined as above) against a particularly relevant microorganism, namely methicillin-resistant *Staphylococcus aureus* (MRSA). MRSA is a bacterium responsible for several infections particularly difficult to treat, to the extent that it is sometimes referred to as "multidrug-resistant *Staphylococcus aureus*". In fact, it is resistant to β-lactam antibiotics and to cephalosporins. MRSA infections are particularly challenging in hospitals wherein patients with open wounds or carrying invasive devices (e.g. catheters) are at high risk of contamination.

Procedure.

Figure 5:
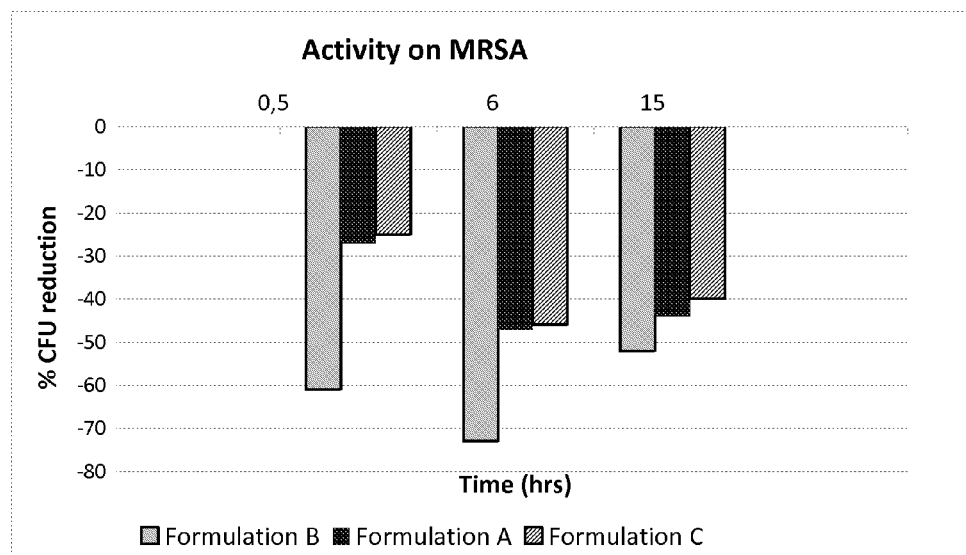
FIG. 5 shows activity of compositions A-C on the growth of methicillin resistant *Staphylococcus aureus* (MRSA) bacteria.

Sterilized fingerpads are contaminated with MRSA ($10^8$ CFU in a 30 microliter volume); contaminated areas are allowed to dry in the air for 3 minutes, then the product to be tested (composition A, B or C) is applied from a distance of about 15 cm for 5 seconds, with a 3 seconds interval, twice. Every formulation is contacted with the microorganisms for 30 min, 3 h, 6 h or 15 h in a moistened chamber. At the end, the fingerpads are dipped for 1 minute in a neutralizing medium to block the antimicrobic action and to collect the microorganisms. A sample of the neutralizing medium is suitably diluted and seeded on an appropriate solid medium. CFU are quantified after 25 h of culture and the resulting data are disclosed in FIG. 5. It is clear that, in line with the results of Experiment 1, the activity of composition C is completely superimposable to that of composition A. Surprisingly, composition B, comprising "sponge like" micronized metallic silver and HA with weight average MW 200 kD, has a remarkably superior effect, reducing the microbial population more substantially both at 30 min and at later points in time. This aspect is particularly remarkable, considering that the amount of silver of composition B is less than half of that of formulation C.

Conclusion: all the tested formulations are effective also against methicilin-resistant *Staphilococcus aureus* (MRSA), but composition B comprising "sponge like" micronized metallic silver and HA with weight average MW 160-200 kDa is substantially more efficient. The activity of the composition comprising "sponge like" micronized metallic silver and HA with weight average MW 160-200 kDa is particularly surprising, considering that the amount of silver in this composition is less than half of that in the commercially available composition.

In view of the results of experiment 2 and 2a, the cytotoxic effect of the formulations is tested against cutaneous fibroblasts, to verify if the presence of silver nullified the effect exerted by 160-200 kDa weight average MW HA on fibroblast proliferation, demonstrated in experiment 1.

Experiment 3

Activity of the Formulation of the Invention on Proliferation of Healthy Fibroblasts from Human Skin Biopsies In Vitro Isolation and culture of fibroblasts were performed according to the procedure described in experiment 1. Cell proliferation was evaluated through the bromodeoxyuridine BrdU labelling test (Bromodeoxyuridine Kit, BioAssay™). Briefly, after incorporation of BrdU, cells are subjected to labelling with an anti-BrdU antibody and then analyzed through a suitable reader.

Samples: given the surprising efficiency of formulation B against MRSA, for formulation convenience, formulation B (based on micronized "sponge like" metallic silver and HA with weight average 160-200 kDa) was selected to be compared with formulation C (marketed product), preparing samples at different concentrations (5 mg/ml; 30 mg/ml) as follows.

Suitable amounts of each formulation were weighted, dissolved in DMEM (cell culture medium) containing BrdU, and kept under shaking for 10 min. Then the mixture was centrifuged at 6000 rpm for 3 min. The supernatant thus obtained was put in contact with the cultured cells, evaluating fibroblast proliferation versus cells in DMEM with BrdU only (control).

Results of the experiment are summarized in FIG. 4 where the first column represents values of cell proliferation after 3 days of incubation, and the second after 5 days of incubation.

It appears immediately clear that formulation B exerts a positive effect on fibroblast proliferation in comparison with the control, regardless of the amount of active ingredients contained in it. The effect evaluated versus control is more substantial for the 5 mg/ml sample and after 3 days of contact, but also for the 30 mg/ml sample significant cell growth is observed at both 3 and 5 days, always in comparison with the control.

Notably, with reference to FIG. 4 third column, growth of fibroblast with respect to the control sample is observed in a test using 30 mg/ml of composition B (comprising 2% w/w micronized "sponge like" silver and 0.2% sodium hyaluronic acid with weight average molecular weight 160-200 kDa). Instead (FIG. 4, fourth column), a reduction of fibroblasts with respect to the control is observed using 5 mg/ml of composition C which comprises 4.25% colloid silver, i.e. a lower overall amount of silver (approximately one third) with respect to the amount used in the test with composition B at 30 mg/ml.

Once again, 160-200 kDa weight average MW HA demonstrates its unexpected properties on cell proliferation also when associated with an antibacterial/antifungal agent. The data of these experiments, in fact, demonstrate that 160-200 kDa weight average MW hyaluronic acid protects the fibroblasts from the cytotoxic activity of silver while leaving unaltered the antimicrobial activity of micronized silver or collidal silver. Data for formulation C, instead, show an opposite trend; already at the concentration of 5 mg/ml at 5 days we have negative proliferation values in comparison with the control, to indicate inhibition of fibroblast proliferation, while with the sample containing 30 mg/ml a decrease of the number of fibroblasts is observed already after 3 days of treatment, clearly indicating toxicity of the sample. Only the 5 mg/ml sample after 5 days of treatment still has a number of fibroblasts identical to the control, but such result is absolutely irrelevant when compared to the equivalent formulation B that, in the same conditions of concentration and time of treatment, increases fibroblast proliferation by over 50%.

Also in view of the experimental data disclosed herewith, the composition of the invention comprising hyaluronic acid and silver, in the form of dry spray, cutaneous foam or hydrophilic gel, is suitable for topical treatment of cutaneous lesions and/or wounds of various origin (acute, chronic, ulcerations of various aetiology, burns, sores) also with exudate, and then characterized by a high risk of infection by, for example, microorganisms such as *Escherichia coli, Pseudomonas aeruginosa, Staphilococcus aureus* and *Enterococcus faecium* and fungi such as *Candida albicans*. The hyaluronic acid used has a weight average MW comprised between 130 and 230 kDa, preferably comprised between 145 and 210 kDa, and even more preferably comprised between 160 and 200 kDa. Its concentration in the final composition can range between 0.1 and 2% by weight (w/w), preferably between 0.1 and 0.5% w/w and even more preferably it is equal to 0.2% w/w. Silver, it can be in colloidal metallic form or in micronized "sponge like" metallic form, with the latter form being preferred, in view of the above advantages. Silver concentration in the final composition can be comprised between 1 and 3% w/w; with the preferred concentration being equal to 2% w/w. Concerning pharmaceutical forms, hydrogel is particularly useful for quite superficial cutaneous lesions and/or wounds; dry spray finds particular use with flat or little cavitated cutaneous lesions and/or wounds, while cutaneous foam is suitable for application on cavitated cutaneous lesions and/or wounds.

In case of dry spray and cutaneous foam, the composition according to the invention comprises propellants as n-butane or a mixture consisting of n-butane, isobutane and propane; in particular, n-butane is preferable in dry spray formulation, whereas the n-butane, isobutane and propane mixture is the propellant of choice for cutaneous foam.

For illustrative purposes, formulations and method of preparation of the chosen pharmaceutical forms are provided herein, which however can be modified according to the knowledge of the person skilled in the art of formulation.

Dry Spray Comprising Colloidal Metallic Ag: 100 g of product contain

| Components | Amount | Function |
| --- | --- | --- |
| Sodium hyaluronate (sodium HA) MW 160-200 kDa | 0.20 | |
| Colloidal metallic silver | 2.0 | Antibacterial |
| Silicon dioxide (Syloid 244) | 4.0 | Suspending agent |
| Light kaolin | q.s. to 100 | Vehicle |
| n-Butane 1.3 | | Propellant |

Micronized and sieved hyaluronic acid is mixed by progressive dilution with previously micronized colloidal silver. The premixture obtained is mixed by progressive dilution with silicon dioxide. The mixture thus obtained is last mixed with light kaolin until homogeneous.

The intermediate product obtained in the above described way then is subjected to distribution in pressurized cylinders.

Dry Spray Comprising Micronized "Sponge Like" Metallic Ag: 100 g of product contain

| Components | Amount | Function |
| --- | --- | --- |
| Sodium hyaluronate (sodium HA) MW 160-200 kDa | 0.20 | |
| Micronized metallic silver (MicroSilver BG ™ Pharma) | 2.0 | Antibacterial |

-continued

| Components | Amount | Function |
|---|---|---|
| Silicon dioxide (Syloid 244) | 4.0 | Suspending agent |
| Light kaolin | q.s. to 100 | Vehicle |
| n-Butane 1.3 | | Propellant |

Micronized and sieved hyaluronic acid is mixed by progressive dilution with sponge-like micronized metallic silver, already having micron particle size. The premixture obtained is mixed by progressive dilution with silicon dioxide. The mixture thus obtained is last mixed with light kaolin until homogeneous.

The intermediate product obtained in the above described way then is subjected to distribution in pressurized cylinders.

Cutaneous Foam Based on Colloidal Metallic Silver: 100 g of product contain

| Components | Amount (g) |
|---|---|
| Sodium hyaluronate (sodium HA) MW 160-200 kDa | 0.20 |
| Colloidal metallic silver | 2.0 |
| Glycerol | 6.0 |
| Caprylocaproyl Macrogolglycerides (Labrasol) | 10.0 |
| Hydrogenated soybean lecithin | 0.3 |
| Polysorbate 80 | 2.0 |
| Benzyl alcohol | 0.5 |
| Potassium sorbate | 0.1 |
| A-Tocopheryl acetate | 0.1 |
| Purified water | q.s. to 100 |
| Isobutane, n-butane, propane | Propelling mixture |

A dispersion of previously micronized colloidal silver in Labrasol is added under shaking to a solution comprised of sodium hyaluronate and glycerol and is mixed until homogeneous. Potassium sorbate, benzyl alcohol, polisorbate 80, alfa-tocoferyl acetate, hydrogenated soybean lecithin are added and shaken until dissolved. Purified water is added until the final volume is reached and shaken until homogeneous. The obtained preparation is filtered and is subjected to distribution in pressurized containers.

Cutaneous Foam Based on Micronized "Sponge Like" Metallic Silver: 100 g of product contain:

| Components | Amount (g) |
|---|---|
| Sodium hyaluronate (sodium HA) 160-200 kDa | 0.20 |
| Micronized metallic silver (MicroSilver BG ™ Pharma) | 2.0 |
| Glycerol | 6.0 |
| Caprylocaproyl Macrogolglycerides (Labrasol) | 10.0 |
| Hydrogenated soybean lecithin | 0.3 |
| Polysorbate 80 | 2.0 |
| Benzyl alcohol | 0.5 |
| Potassium sorbate | 0.1 |
| A-Tocopheryl acetate | 0.1 |
| Purified water | q.s. to 100 |
| Isobutane, n-butane, propane | Propelling mixture |

A dispersion of micronized "sponge like" metallic silver in Labrasol is added under shaking to a solution comprised of sodium hyaluronate and glycerol and is mixed until homogeneous. Potassium sorbate, benzyl alcohol, polisorbate 80, alfa-tocoferyl acetate, hydrogenated soybean lecithin are added and shaken until dissolved. Purified water is added until the final volume is reached and shaken until homogeneous. The obtained preparation is filtered and is subjected to distribution in pressurized containers.

Hydrophilic Gel Comprising Colloidal Metallic Silver: 100 g of product contain:

| Components | Amount (g) |
|---|---|
| Sodium hyaluronate (sodium HA) 160-200 kDa | 0.20 |
| Colloidal metallic silver | 2.0 |
| Carbomer 974P | 1.5 |
| Glycerol | 10.0 |
| Propylene glycol | 6.675 |
| Triethanolamine | 1.325 |
| PEG 400 | 6.675 |
| Methyl-p-hydroxybenzoate | 0.2 |
| Propyl-p-hydroxybenzoate | 0.02 |
| Purified water | q.s. to 100 |

Methyl-p-hydroxybenzoate and propyl-p-hydroxybenzoate are dissolved in purified water at 80° C. After cooling the solution to room temperature, sodium hyaluronate is added and mixed until dissolution is complete. Then PEG 400 is dissolved and Carbomer 974P is added keeping under shaking until homogeneous dispersion and complete hydration of the latter are obtained. Then triethanolamine is added until gelation of the aqueous phase is obtained. Last, under shaking, glycerol, propylene glycol and previously micronized colloidal silver are added and mixed until homogeneous.

Hydrophilic Gel Comprising Micronized "Sponge Like" Metallic Silver: 100 g of product contain:

| Components | Amount (g) |
|---|---|
| Sodium hyaluronate (sodium HA) 160-200 kDa | 0.20 |
| Micronized metallic silver (MicroSilver BG ™ Pharma) | 2.0 |
| Carbomer 974P | 1.5 |
| Glycerol | 10.0 |
| Propylene glycol | 6.675 |
| Triethanolamine | 1.325 |
| PEG 400 | 6.675 |
| Methyl-p-hydroxybenzoate | 0.2 |
| Propyl-p-hydroxybenzoate | 0.02 |
| Purified water | q.s. to 100 |

Methyl-p-hydroxybenzoate and propyl-p-hydroxybenzoate are dissolved in purified water at 80° C. After cooling the solution to room temperature, sodium hyaluronate is added and mixed until dissolution is complete. Then PEG 400 is dissolved and Carbomer 974P is added keeping under shaking until homogeneous dispersion and complete hydration of the latter are obtained. Then triethanolamine is added until gelation of the aqueous phase is obtained. Last, under shaking, glycerol, propylene glycol and micronized "sponge like" metallic silver are added and mixed until homogeneous.

In summary, it was found that a formulation comprising HA with a weight average MW between 130 and 230 kDa, preferably 145 to 210 kDa and more preferably from 160 to 200 kDa, with silver in concentration 2% w/w is capable of eliminating potentially pathogenic bacteria and can be effectively used in topic therapy for treatment of cutaneous lesions and wounds originating, for example, from cutaneous lesions and/or wounds of various origin in form of dry spray or cutaneous foam or hydrophilic gel. Silver in the composition of the invention can be in colloidal metallic form or in micronized "sponge like" metallic form, with the latter form being preferred, in view of its surprisingly higher activity against MRSA infections.

The invention claimed is:

1. A composition comprising hyaluronic acid and silver, wherein the hyaluronic acid has an average weight molecular weight between 130 and 230 Kda and wherein the silver has a micronized metallic form with a porous sponge structure with a mean particle size between 2 and 18 micrometers and a surface area not less than 5 $m^2/g$ or a colloidal metallic form.

2. The composition according to claim 1 wherein the hyaluronic acid has an average weight molecular weight between 145 and 210 Kda.

3. The composition according to claim 1 wherein the hyaluronic acid has an average weight molecular weight between 160 and 200 Kda and the silver has a micronized metallic form with a porous sponge structure.

4. The composition according to claim 1 wherein the hyaluronic acid has an average molecular weight between 160 and 200 Kda and the silver has a colloidal metallic form.

5. The composition according to claim 1, wherein the hyaluronic acid has a concentration between 0.1 and 2% w/w of the total composition.

6. The composition according to claim 5, wherein the hyaluronic acid has a concentration between 0.1 and 0.5% w/w of the total composition.

7. The composition according to claim 6, wherein the hyaluronic acid has a concentration of 0.2% w/w of the total composition.

8. The composition according to claim 1, wherein the silver in a micronized metallic form with a porous sponge structure or the silver is in a colloidal metallic form at a concentration from 1 to 3% w/w of the total composition.

9. The composition according to claim 8, wherein the silver has a concentration of 2% w/w of the total composition.

10. A pharmaceutical formulation comprising the composition according to claim 1, and at least one pharmaceutically acceptable excipient.

11. The pharmaceutical formulation according to claim 10, wherein the at least one excipient is selected from a suspending agent, a vehicle and a propellant.

12. The pharmaceutical formulation according to claim 11, in which the propellant is selected from a group consisting of isobutane/n-butane/propane mixtures and n-butane.

13. The pharmaceutical formulation according to claim 10 in the form of a dry spray, a foam or a hydrophilic gel suitable for cutaneous application.

14. The pharmaceutical formulation according to claim 13 in the form of a dry spray, comprising hyaluronic acid with an average weight molecular weight between 160 and 200 kDa at 0.2% w/w concentration, silver in metallic micronized form with a porous sponge structure at a concentration of 2% w/w and n-butane as propellant.

15. The pharmaceutical formulation according to claim 13 in the form of a dry spray, comprising hyaluronic acid with an average weight molecular weight from 160 to 200 kDa at a concentration of 0.2% w/w, silver in colloidal metallic form 2% w/w concentration and n-butane as propellant.

16. The formulation according to any one of claims 13-15 in the form of a dry spray which lays as transparent gel on the cavity of the lesion to promote the optimal moist wound healing.

17. The pharmaceutical formulation according to claim 13 in the form of a foam, comprising hyaluronic acid with an average weight molecular weight between 160 and 200 kDa at a concentration of 0.2% w/w, silver in metallic micronized form with a porous sponge structure or in colloidal metallic form at a concentration of 2% w/w and a isobutane/n-butane/propane mixture as propellant.

18. The pharmaceutical formulation according to claim 13 in the form of a hydrophilic gel, comprising hyaluronic acid with an average weight molecular weight from 160 to 200 kDa at a concentration of 0.2% w/w, silver in metallic micronized form with a porous sponge structure or in colloidal metallic form at a concentration of 2% w/w.

19. The composition according to claim 1 or formulation according to claim 10 formulated for topical use.

20. The pharmaceutical formulation according to claim 14 formulated for topical use.

21. The pharmaceutical formulation according to claim 15 formulated for topical use.

22. The pharmaceutical formulation according to claim 17 formulated for topical use.

23. The pharmaceutical formulation according to claim 18 formulated for topical use.

* * * * *